United States Patent
Uchida et al.

(10) Patent No.: US 6,596,696 B1
(45) Date of Patent: Jul. 22, 2003

(54) MALTO-OLIGOSACCHARIDE DERIVATIVES AND USES THEREOF

(75) Inventors: Riichiro Uchida, Noda (JP); Ayako Nasu, Noda (JP); Yukihiko Iwai, Noda (JP); Takao Someya, Noda (JP); Koichiro Tobe, Noda (JP)

(73) Assignee: Kikkoman Corporation, Noda (JP)

( * ) Notice: Subject to any disclaimer, the term of this patent is extended or adjusted under 35 U.S.C. 154(b) by 0 days.

(21) Appl. No.: 09/913,880

(22) PCT Filed: Jan. 31, 2000

(86) PCT No.: PCT/JP00/00512
§ 371 (c)(1),
(2), (4) Date: Aug. 17, 2001

(87) PCT Pub. No.: WO00/50434
PCT Pub. Date: Aug. 31, 2000

(30) Foreign Application Priority Data

Feb. 22, 1999 (JP) ............................................. 11-042695

(51) Int. Cl.[7] .................... A61K 31/70; A61K 31/7042; A61K 31/7052; A61K 31/715; C07H 17/02
(52) U.S. Cl. .......................... 514/27; 514/54; 536/17.4; 536/17.3; 536/17.2; 536/123.1; 536/22.1
(58) Field of Search .................... 536/4.1, 17.2, 536/17.3, 17.4, 123.1, 22.1; 514/25, 54, 27

(56) References Cited

FOREIGN PATENT DOCUMENTS

| | | |
|---|---|---|
| JP | 9-278789 | 10/1997 |
| JP | 09/278789 | * 10/1997 |

OTHER PUBLICATIONS

R. Uchida, et al. "Synthesis of new 1–10 N–containing malto–oligosaccharides,. alpha.–amylase inhibitors, and their biological activities", Chem. Pharm. Bull (1999), 47(2), 187–193.

European Search Report May 21, 2002.

New enzymatic synthesis of $6^3$–modified maltooligosaccharides and their inhibitory activities for human α–amylases, Riichiro Uchida, et al., Elsevier Science Ltd., Carbohydrate Research, vol. 307 (1998), pp 69–76.

* cited by examiner

Primary Examiner—Samuel Barts
Assistant Examiner—Michael C. Henry
(74) Attorney, Agent, or Firm—Banner & Witcoff, Ltd.

(57) ABSTRACT

Maltoligosaccharide derivatives represented by the general formula:

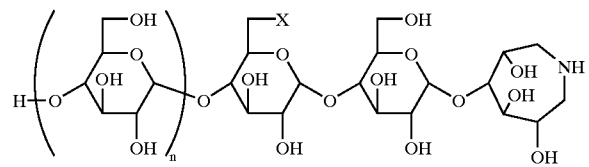

wherein n is an integer of 0 to 3 and X is a hydrogen atom or a hydrophobic group) or their hydrates or physiologically acceptable salts, and an α-amylase inhibitor and a prophylactic or therapeutic agent for hyperglycemia such as diabetes containing them as an active ingredient.

12 Claims, No Drawings

MALTO-OLIGOSACCHARIDE DERIVATIVES AND USES THEREOF

This is a U.S. National Phase Application Under 35 USC 371 and applicant herewith claims the benefit of priority of PCT/JP00/00512 filed Jan. 31, 2000, in the Japanese Patent Office and Application No. 11-042695 filed in Japan on Feb. 22, 1999 each of whose contents are incorporated by reference.

TECHNICAL FIELD

The present invention relates to maltoligosaccharide derivatives having a specific molecular structure and their uses. More particularly, it relates to an α-amylase inhibitor and the pharmaceuticals useful for the prophylaxis and treatment of hyperglycemia, for example, diabetes and their complications, which contain said derivatives as an active ingredient.

BACKGROUND ART

Carbohydrates ingested by mammals are digested (hydrolyzed) to some extent by salivary α-amylase in the oral cavity and stomach, and then digested thoroughly by pancreatic α-amylase in the duodenum and jejunum to become oligosaccharides or disaccharides. Then they are further hydrolyzed by a glucoside-hydrolaze such as glucoamylase and maltase to finally become a monosaccharide such as glucose which is absorbed from the fimbriae on the intestinal membranes. After ingestion of carbohydrates, there takes place a primary increase in blood glucose level, or so-called hyperglycemic symptom, due to the absorption of glucose, but this abnormal phenomenon is usually remedied in due course as the blood glucose level is brought back to a normal range and controlled to stay therein by the homeostasis maintaining system in the living body.

However, if a person suffers an alimentary hyperglycemic symptom for a long time or has abnormality in carbohydrate metabolism, such as an abnormal rise of blood glucose level, he or she is liable to a disease called hyperglycemia, which leads to obesity or diabetes. Obesity is caused as the hyperglycemic condition resulting from overeating incites much secretion of insulin to promote fat synthesis and to decrease lipolysis, inducing accumulation of fat in the body. On the other hand, diabetes is caused as the promoted secretion of insulin by the hyperglycemic condition resulting from overeating invites a reduction of sensitivity of the insulin receptors or fatigue of the β cells of the pancreatic Langerhans islet. It is known that obesity and diabetes tend to provoke many serious complications such as hyperlipidemia, hypertension, arteriosclerosis, autonomic imbalance, and cataract.

As a potent therapeutic agent for such hyperglycemia, certain digestive enzyme inhibitors, for example, "Basen" containing Voglibose (produced by Takeda Chemical Industries Co., Ltd.) and "Glucobay" containing Acarbose (produced by Bayer Chemical Corp.), are clinically used. Both of these compounds, however, have the disadvantage of inciting such side effects as causing abdominal distention, meteorism, increase of flatus, loose passage, diarrhea, abdominal pain, etc., because of their strong inhibitory action against glucosidase. Also, the maltoligosaccharide derivatives which the present inventors had previously proposed (JP-A-9-278789) are not necessarily satisfactory in certain respects, such as strength of their amylase inhibitory activity.

DISCLOSURE OF THE INVENTION

The present invention is intended to provide a chemical substance which is free of said defects of the conventional therapeutic and prophylactic agents for hyperglycemia and capable of strongly inhibiting human α-amylase to work effectively for the prophylaxis and treatment of hyperglycemia, for example diabetes and the diseases induced thereby, and an α-amylase inhibitor and prophylactic and therapeutic agents for hyperglycemia containing said substance as an active ingredient.

The inventors extensively studied for attaining the above object, and found that the maltoligosaccharide derivatives produced by converting the reduced terminal glucose of oligosaccharides into hexahydro-1H-azepine-3R, 4R, 5R, 6S-tetrol and also converting the 6-position of the 3rd glucose residue (as counted from the hexahydro-1H-azepine-3R, 4R, 5R, 6S-tetrol) into a hydrophobic group, and their hydrates or their physiologically acceptable salts strongly inhibit α-amylase derived from human pancreatic juice (hereinafter referred to as HPA) and α-amylase derived from human salivary gland (hereinafter referred to as HSA) and also act to suppress or retard digestion and absorption of glucose, and that it is possible to overcome the said defects of the prior art by using these compounds as an active ingredient of the therapeutic and prophylactic agents for hyperglycemia. The present invention has been attained on the basis of the above finding.

According to the present invention, there are provided the maltoligosaccharide derivatives represented by the following general formula (1):

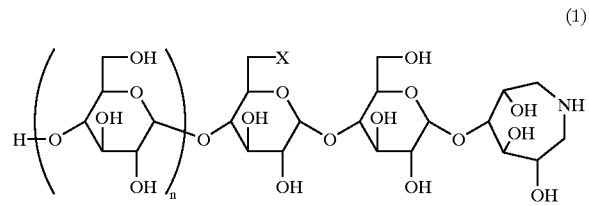

(wherein n is an integer of 0 to 3, and X is a hydrogen atom or a hydrophobic group) or their hydrates or physiologically acceptable salts; an α-amylase inhibitor containing one of said maltoligosaccharide derivatives of the formula (1) or their hydrates or physiologically acceptable salts as an active ingredient; and a prophylactic or therapeutic agent for hyperglycemia containing one of said maltoligosaccharide derivatives of the formula (1) or their hydrates or physiologically acceptable salts as an active ingredient. The present invention is explained in detail.

BEST MODE FOR CARRYING OUT THE INVENTION

The maltoligosaccharide derivatives according to the present invention (hereinafter referred to as the present derivatives) are those which are represented by the general formula (1) as mentioned above wherein n is an integer of 0 to 3 and X is a hydrogen atom or a hydrophoblic group. The present derivatives include their hydrates and physiologically acceptable salts. The hydrophobic group represented by X can be, for instance, a halogen atom such as fluorine, chlorine, b romine and iodine atom, a substituted or non-substituted alkyloxy group, a substituted or non-substituted alkylthio group, a substituted or non-substituted alkylsulfonyl group, a substituted or non-substituted alkylcarbamoyl, or azido group.

In use of the present derivatives for producing an α-amylase inhibitor or a prophylactic or therapeutic agent for hyperglycemia, it is desirable, for the reasons stated below, that in the formula (1) n is 0 to 3, especially 0 or 1, and X is a hydrogen atom or a halogen atom, especially a hydrogen atom.

The present derivatives can be synthesized efficiently from, for instance, $6^3$-modified maltoligosaccharides represented by the general formula (2):

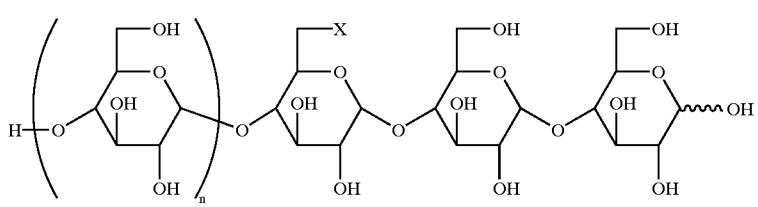

(2)

(wherein n is an integer of 0 to 3, and X is a hydrogen atom or a hydrophobic group). In the formula (2), n is an integer of 0 to 3, and X is a hydrogen atom or a hydrophobic group. The hydrophobic group can be, for instance, a halogen atom such as fluorine, chlorine, bromine and iodine atom, a substituted or non-substituted alkyloxy group, a substituted or non-substituted alkylthio group, a substituted or non-substituted alkylsulfonyl group, a substituted or non-substituted alkylcarbamoyl, or azido group. Said $6^3$-modified maltoligosaccharides can be synthesized, for instance, by a method described in Carbohydrate Research, Vol. 307, pp. 69–76, 1998.

A $6^3$-modified maltologosaccharide synthesized by the above method is reacted with, for instance, p-toluenesulfonyl chloride in pyridine, and if necessary $6^1$-tosyl-$6^3$-modified maltoligosaccharide are separated by a conventional method and reacted with sodium azide in N,N-dimethylformamide (DMF) to give $6^1$-azido-$6^3$-modified maltoligosaccharides. These $6^1$-azido-$6^3$-modified maltoligosaccharides are separated from each other by a known method, and the latter is reduced by introducing hydrogen gas in the presence of palladium carbon to produce the present derivative represented by the formula (1).

The thus obtained present derivative can be purified by a conventional method, for example, precipitation using a pertinent organic solvent or column chromatography using an ion exchange resin, aminopropyl silica gel, silica gel, active carbon, etc.

The present derivatives represented by the formula (1), obtained in the manner described above, have a strong inhibitory acitivity against HPA and HSA as explained below. In comparison with the maltoligosaccharide derivatives of the formula (1) wherein X is a non-modified group (OH group), which the present inventors had previously proposed (JP-A-9-278789), the present derivatives in which a hydrogen atom or a hydrophobic group has been introduced to the X position are remarkably enhanced in amylase inhibitory activity. Also, the above-mentioned prior art maltoligosaccharide derivatives or their hydrates or physiologically acceptable salts, although having an action to suppress the blood glucose level after meal, are susceptible to decomposition in the intestinal tracts and may therefore be greatly weakened in their activity. In contrast, the present derivatives, since X is modified, are enhanced in their amylase inhibitory activity and not easily decomposed in the intestinal tracts, so that their activity keeps long in the intestinal tracts. Consequently, a high blood glucose level suppressing effect after meal can be obtained by a small dosage of the compound. In view of affinity with amylase, the present derivatives represented by the formula (1) are preferably those in which in the formula (1) n is 0 to 3, especially 0 or 1, and X is a hydrogen atom or a halogen atom, especially a hydrogen atom.

As explained above, the present derivatives have a strong inhibitory activity against α-amylase, so that a potent α-amylase inhibitor can be obtained by using such derivatives as an active ingredient. Further, the present derivatives having such an inhibitory activity also depress carbohydrate metabolism of animals, so that they can check the increase in blood glucose level and are therefore useful as a prophylactic or therapeutic agent for hyperglycemia, for example, diabetes, adiposity and the diseases caused thereby, such as hyperlipidemia, fatty liver, autonomic imbalance, arteriosclerosis, cataract, etc. The present derivatives are especially useful for the prophylaxis and treatment of diabetes.

Nontoxic salts obtained by reacting the present derivatives with a pharmacologically acceptable acid or base in the usual method can also be used for the preparation of the α-amylase inhibitor or prophylactic or therapeutic agents for hyperglycemia according to the present invention. The acids usable for the above reaction include inorganic acids such as hydrochloric acid, hydrobromic acid, sulfuric acid, phosphoric acid and nitric acid, and organic acids such as acetic acid, malic acid, citric acid, ascorbic acid, mandelic acid and methanesulfonic acid. The bases include sodium hydroxide, potassium hydroxide, ammonium hydroxide, calcium hydroxide, etc.

The α-amylase inhibitor and the prophylactic or therapeutic agent for hyperglycemia according to the present invention can be obtained by using the present derivatives either singly or as a combination of two or more of them as an active ingredient. Also, the α-amylase inhibitor and the prophylactic or therapeutic agent for hyperglycemia according to the present invention may comprise the present derivative alone or may further contain other compounding agent(s) such as excipient, lubricant, diluent, stabilizer, pH adjuster, antiseptic, sweetener, aromatic, flavor, colorant, preservative, emulsifier, thickening agent, and base materials to provide the preparations of various dosage forms such as tablet, powder, granule, capsule, syrup, sappository, injection and drops. Conventional methods can be used for making these preparations. As excipient, ordinarily used potato starch, lactose, crystal cellulose, mannitol and the like may be used. As lubricant, magnesium stearate, talc, hard oil and the like may be used. As sweetener, aromatic and flavor, there may be used common salt, saccharin, orange oil, citric acid, menthol, malic acid, etc.

The dosage of the α-amylase inhibitor, prophylatic or thermapeutic agent for hyperglycemia, and prophylatic or thermapeutic agent for diabetes according to the present invention is variable depending on the route of administration, condition of the disease, patient's age and body weight, and other factors, but usually it is selected from within the range of 10 to 3,000 mg, preferably 100 to 600 mg (as the present derivative) per day for the adult. The route of administration may be either oral or parenteral, but oral administration is advantageous. The present derivative may be contained, either alone or in combination with other compounding agent(s) such as mentioned above, in foods such as coffee, soft drinks, fruit juice, jam and biscuits to provide health foods having an α-amylase inhibitory effect.

The present invention is further illustrated by showing examples and referential examples, but the present invention is not limited by these examples in any way.

REFERENTIAL EXAMPLE 1

Production of O-(6-Deoxy-α-D-glucopyranosyl)-(1→4)-O-(α-D-glucopyranosyl)-(1→4)-6-O-p-toluenesulfonyl-D-glucopyranose $6^3$-deoxymaltotriose (15 g, 31 mmol) was dissolved in pyridine (450 ml), to which tosyl chloride (8.8 g, 46 mmol) was added and the mixture was reacted with stirring under cooling with ice water for 3 hours. After the completion of the reaction, the reaction was stopped by adding distilled water (75 ml) and the solution was evaporated to dryness. The residue was dissolved in a small quantity of distilled water and this solution was purified by ODS column chromatography ($H_2O$→50% $CH_3CN$, gradient). The fraction containing the objective compound was concentrated and then lyophilized to obtain colorless powder (2.8 g, 4.3 mmol, yield: 14%).

m.p. 125–127° C. (dec.), [α]+127° (c0.25, $H_2O$), IR(KBr) cm$^{-1}$: 3330, 2930, 1650, 1600, 1360, and 1050, $^1$H-NMR ($D_2O$) δ: 1.29 (d, 3H, J=6.4 Hz, H-6c), 2.48 (s, 3H, —$SO_2PhCH_3$), 3.12–4.06 (m, H-2–6), 4.59 (d, 0.5H, J=7.8 Hz, αH-1a), 5.12 (d, 0.5H, J=3.7 Hz, βH-1a), 5.25 and 5.34 (d, each 1H, J=3.1 and 3.9 Hz, H-1b–c), 7.53 (d, 2H, J=8.8 Hz, H-3 and H-5 of —$SO_2PhCH_3$), 7.83 (d, 2H, J=8.5 Hz, H-2 and H-6 of —$SO_2PhCH_3$), $^{13}$C-NMR ($D_2O$) δ: 19.44 (—$CH_3$), 23.67 (—$SO_2PhCH_3$), 94.72 and 98.69 (C-1a), 102.17 and 103.11 (C-1b–c), 130.51 and 133.06 (—$SO_2PhCH_3$), tR (TSKgel Amide-80, eluent: 8:2 (v/v) $CH_3CN$—$H_2O$): 7.7 min., Anal. Calcd. for $C_{25}H_{38}O_{17}S \cdot 1.33H_2O$: C, 45.04; H, 6.15, Found: C, 45.15; H, 5.98.

REFERENTIAL EXAMPLE 2

Production of O-(6-Deoxy-α-D-glucopyranosyl)-(1→4)-O-(α-D-glucopyranosyl)-(1→4)-6-azido-6-deoxy-D-glucopyranose O-(6-deoxy-α-D-glucopyranosyl)-(1→4)-O-(α-D-glucopyranosyl)-(1→4)-6-O-p-toluenesulfonyl-D-glucopyranose (2.2 g, 3.4 mmol) produced in Referential Example 1 was dissolved in DMF (40 ml), to which $NaN_3$ (10 mol eq.) was added and the mixture was reacted with stirring at 80° C. for 2 hours. After the completion of the reaction, the solvent was distilled off under reduced pressure and the residue was purified by ODS chromatography ($CH_3CN/H_2O$=5/95 (v/v)). The fraction containing the objective compound was concentrated and then lyophilized to obtain colorless powder (0.66 g, 1.3 mmol, yield: 38%).

m.p. 131–133° C. (dec.), [α]+174° (c0.25, $H_2O$), IR(KBr) cm$^{-1}$: 3340, 2930, 2110, 1650, 1360, and 1050, $^1$H-NMR ($D_2O$) δ: 1.27 (d, 3H, J=6.1 Hz, H-6c), 3.12–4.01 (m, H-2–6), 4.67 (d, 0.5H, J=8.5 Hz, αH-1a), 5.23 (d, 0.5H, J=3.9 Hz, βH-1a), 5.29 and 5.40 (d, each 1H, J=3.0 and 3.6 Hz, H-1b–c), $^{13}$C-NMR ($D_2O$) δ: 19.34 (—$CH_3$), 53.73 (—$CH_2N_3$), 94.75 and 98.66 (C-1a), 102.26 and 102.77 (C-1b–c), tR (TSKgel Amide-80, eluent: 8:2 (v/v) $CH_3CN$-$H_2O$): 12.8 and 14.4 min., Theoretical ($C_{18}H_{31}N_3O_{14} \cdot H_2O$: C, 40.68; H, 6.26; N, 7.91 Found: C, 40.97; H, 6.00; N, 8.12.

EXAMPLE 1

Production of (3R, 4R, 5R, 6S)-Hexahydro-3,5,6-trihydroxy-1H-azepine-4-yl O-(6-deoxy-α-D-glucopyranosyl)-(1→4)-α-D-glucopyranoside (Hereinafter Referred to as DOG2Az)

O-(6-deoxy-α-D-glucopyranosyl)-(1→4)-O-(α-D-glucopyranosyl)-(1→4)-6-azido-6-deoxy-D-glucopyranose (0.50 g, 0.97 mmol) was dissolved in distilled water (35 ml), to which 10% Pd-C (0.27 g) was added and the mixture was subjected to catalytic reduction under normal pressure with stirring at room temperature for 16 hours. After the completion of the reaction, the catalyst was filtered with Celite, and the residue was concentrated and lyophilized to obtain colorless powder (0.40 g, 0.85 mmol, yield: 88%).

m.p. 132–134° C. (dec.), [α]+133° (c0.25, $H_2O$), IR(KBr) cm$^{-1}$: 3340, 2930, 1650, 1420, and 1050, $^1$H-NMR ($D_2O$) δ: 1.28 (d, 3H, J=6.2 Hz, H-6c), 2.85–3.12 (m, 4H, H-2a and H-7a), 3.55–4.18 (m, H-2–6), 5.17 and 5.31 (d, each 1H, J=3.9 and 3.0 Hz, H-1b–c), $^{13}$C-NMR ($D_2O$) δ: 19.34 (—$CH_3$), 51.76 and 52.08 (—$CH_2NHCH_2$—), 101.78 and 102.65 (C-1b–c), tR (TSKgel Amide-80, eluent: 6:4 (v/v) $CH_3CN$-ammonium formate buffer 25 mM pH8.5):11.3 min., Theoretical ($C_{18}H_{33}NO_{13} \cdot 0.5H_2O$: C, 45.00; H, 7.13; N, 2.92 Found: C, 44.95; H, 6.81; N, 3.00.

REFERENTIAL EXAMPLE 3

Production of O-(α-D-glucopyranosyl)-(1→4)-O-(6-deoxy-α-D-glucopyranosyl)-(1→4)-O-(α-D-glucopyranosyl)-(1→4)-6-azido-6-deoxy-D-glucopyranose $6^3$-deoxymaltotetraose (15 g, 23 mmol) was dissolved in pyridine (450 ml), to which tosyl chloride (8.8 g, 46 mmol) was added and the mixture was reacted with stirring under cooling with ice water for 3 hours. After the completion of the reaction, the reaction was stopped by adding distilled water (75 ml) and the solution was evaporated to dryness. The residue was dissolved in a small quantity of distilled water and this solution was purified by ODS chromatography ($H_2O$→50% $CH_3CN$, gradient). The fraction containing the objective compound was concentrated and then lyophilized to obtain colorless powder of O-(α-D-glucopyranosyl)-(1→4)-O-(6-deoxy-α-D-glucopyranosyl)-(1→4)-O-(α-D-glucopyranosyl)-(1→4)-6-O-p-toluenesulfonyl-D-glucopyranose (2.9 g, 3.6 mmol, yield: 16%).

This tosyl derivative (2.9 g, 3.6 mmol) was dissolved in DMF (40 ml), to which $NaN_3$ (10 mol eq.) was added and the mixture was reacted with stirring at 80° C. for 2 hours. After the completion of the reaction, the solvent was distilled off under reduced pressure, and the residue was purified by ODS chromatography ($CH_3CN/H_2O$=5/95 (v/v)). The fraction containing the objective compound was concentrated and then lyophilized to obtain colorless powder of objective O-(α-D-glucopyranosyl)-(1→4)-O-(6-deoxy-α-D-glucopyranoxyl)-(1→4)-O-(α-D-glucopyranosyl)-(1→4)-6-azido-6-deoxy-D-glucopyranose (2.0 g, 3.0 mmol, yield: 83%).

m.p. 152–154° C. (dec.) [α]+179° (c0.25, $H_2O$), IR(KBr) $cm^{-1}$:3320, 2940, 2110, 1650, 1360, and 1050, $^1$H-NMR ($D_2O$) δ: 1.33 (d, 3H, J=5.9 Hz, H-6c), 3.25–4.01 (m, H-2-6), 4.66 (d, 0.5H, J=8.1 Hz, αH-1a), 5.21–5.40 (m, 3.5H, βH-1a and H-1b–d), $^{13}$C-NMR ($D_2O$) δ: 19.97 (—$CH_3$), 53.85 (—$CH_2N_3$), 94.77 and 98.71 (C-1a), 102.26, 102.31 and 102.65 (C-1b–d), tR (TSKgel Amide-80, eluent: 6:4 (v/v) $CH_3CN$-$H_2O$): 5.6 min., Theoretical ($C_{24}H_{41}N_3O_{19}$·1.33$H_2O$: C, 41.20; H, 6.29; N, 6.01, Found: C, 41.14; H, 6.11; N, 5.92.

EXAMPLE 2

Production of (3R, 4R, 5R, 6S)-Hexahydro-3,5,6-trihydroxy-1H-azepine-4-yl O-(α-D-glucopyranosyl)-(1→4)-O-(6-deoxy-α-D-glucopyranosyl)-(1→4)-α-D-glucopyranoside (Hereinafter Referred to as GDOG2Az)

O-(α-D-glucopyranosyl)-(1→4)-O-(6-deoxy-α-D-glucopyranosyl)-(1→4)-O-(α-D-glucopyranosyl)-(1→4)-6-azido-6-deoxy-D-glucopyranose (150 mg, 0.22 mmol) obtained in Referential Example 3 was dissolved in distilled water (25 ml), to which 10% Pd-C (30 mg) was added and the mixture was subjected to catalytic reduction under normal pressure with stirring at room temperature for 16 hours. After the completion of the reaction, the catalyst was filtered with Celite and the filtrate was purified by ion exchange resin (Dowex 1×4, $OH^-$ form, eluted with $H_2O$). The fraction containing the objective compound was concentrated and then lyophilized to obtain the objective colorless powder (124 mg, 0.20 mmol, yield: 89%).

m.p. 144–146° C. (dec.), [α]+154° (c0.25, $H_2O$), IR(KBr) $cm^{-1}$: 3320, 2910, 1560, 1420, and 1040, $^1$H-NMR ($D_2O$) δ: 1.33 (d, 3H, J=6.3 Hz, H-6c), 2.90–3.10 (m, 4H, H-2a and H-7a), 3.30–4.18 (m), 5.17, 5.31, and 5.39 (d, each 1H, J=3.9, 4.2, and 3.9 Hz, H-1b–d), $^{13}$C-NMR ($D_2O$) δ: 20.07 (—$CH_3$), 51.64 and 51.89 (—$CH_2NHCH_2$—), 101.78, 102.53, and 102.53 (C-1b–d), tR (TSKgel Amide-80, eluent: 6:4 (v/v) $CH_3CN$-ammonium formate buffer 25 mM pH8.5): 13.9 min., Theoretical ($C_{24}H_{43}NO_{18}$·2$H_2O$): C, 43.05; H, 7.07; N, 2.09, Found: C, 42.71; H, 6.74; N, 2.00.

EXAMPLE 3

In vitro Amylase Activity Inhibition test (1) Preparation of Human α-amylase Solution Commercial HPA and HSA were dissolved in purified water to a concentration of 350 IU/l to prepare an α-amylase solution. As commercial HPA and HSA, "Calibzyme AMY" (available from International Reagents Corp. Japan) was used. The α-amylase activity was determined according to the calibration curve of a commercial α-amylase determining reagent "Neo Amylase Test [FDAIICHI]" (available from Daiichi Pure Chemicals Co., Ltd., Japan).

(2) Preparation of Inhibitor Solution

DOG2Az obtained in Example 1, GDOG2Az obtained in Example 2 and comparative G2Az ($6^3$-position non-modified maltoligosaccharide derivative disclosed in JP-A-9-278789) represented by the following formula (3) were diluted with distilled water so that the final concentration would become 5 to 0.0001 mM.

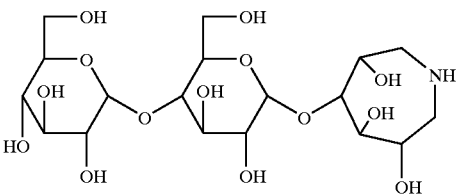

(3) Determination of Human α-amylase Inhibitory Activity (IC50) of Inhibitor Solution 3.0 ml of distilled water, 1.0 ml of the inhibitor solution, Neo Amylase Test [DAIICHI] (produced by Daiichi Pure Chemicals Co., Ltd., Japan) and one tablet of blue starch were added to 100 μl of HPA or HSA solution, and the mixture was stirred by a mixer for about 10 seconds and then heated at 37° C. for 30 minutes. Thereafter, 1.0 ml of 0.5 N sodium hydroxide solution was added and the mixture was further stirred. Then the reaction was stopped, the solution was centrifuged (1,500 G, 5 minutes) and absorbance of the supernatant at 620 nm was measured. In blank, distilled water was used in place of the inhibitor solution. Results are shown in Table 1. "IC50" indicates the final concentration (mM) of the inhibitor material required for inhibiting the activity of HPA or HSA solution by 50%.

TABLE 1

| Inhibitor | IC50 (mM) HPA | IC50 (mM) HSA |
| --- | --- | --- |
| G2Az (Comparison) | 0.043 | 0.082 |
| DOG2Az (Example) | 0.024 | 0.037 |
| GDOG2Az (Example) | 0.026 | 0.028 |

It is seen from Table 1 that the maltoligosaccharide derivatives of the present invention have a saliently strong inhibitory action against HPA and HSA in comparison with the compound used for comparison.

EXAMPLE 4

(Anti-diabetic Action of α-amylase Inhibitor (1) Test Animal

Commercially available healthy mice (Crj:CD-1(ICR) with body weight of 20.5 to 26.0 g, bred by Japan Charles Liver Co., Ltd.), were used for the test.

(2) Test Method

The mice were divided into three groups (n=5). After left fasting for 20 hours, the mice of the compound-administered groups were forced to take orally DOG2Az, G2Az and corn starch as saccharide which was made into a liquid state with sterilized distilled water. The test groups and the amounts of the materials given to the respective groups are shown in Table 2.

TABLE 2

| Test groups | Materials given and amounts | Number of mice |
| --- | --- | --- |
| Group 1 | Corn starch (2,000 mg/kg) | 5 |
| Group 2 | Corn starch (2,000 mg/kg) + G2Az (60 mg/kg) | 5 |
| Group 3 | Corn starch (2,000 mg/kg) + DOG2Az (5 mg/kg) | 5 |

Blood was collected from the orbital vein of each mouse before and after the intake of the materials (0 and after 30 minutes), and the amount of glucose in blood was measured to determine the inhibitory effect against the rise of blood glucose level, i.e. anti-diabetic action of the compounds, after intake of corn starch. Results are shown in Table 3. The inhibitory effect against the rise of blood glucose level was judged by t-test. Glucose concentration in blood was measured by a blood glucose level analyzer "ANTSENSE" (mfd. by Bayer Sankyo Ltd.).

TABLE 3

|  | Blood glucose level before intake | Blood glucose level 30 minute after intake | Significant test |
| --- | --- | --- | --- |
| Control group | 93 ± 9 | 299 ± 49 |  |
| G2Az-administered group (60 mg/kg) | 102 ± 21 | 169 ± 8 | P < 1% |
| DOG2Az-administered group (5 mg/kg) | 101 ± 18 | 136 ± 23 | P < 0.1% |

As is seen from Table 3, in the group to which DOG2Az, a derivative of the present invention, was given, the rise of blood glucose level was suppressed significantly in comparison with the control group, which indicates efficacy of DOG2Az as a prophylactic or therapeutic agent for diabetes. It is also noted that the present derivative, as compared with G2Az, $6^3$-position non-modified compound used for comparison, shows a high inhibitory activity excelling that of G2Az at a lower dosage.

Examination of excreta from the mice which had taken the present compound showed no sign of side effects such as diarrhea or loose passage of the compound.

EXAMPLE 5

Lyophilized Powder 240 g of DOG2Az obtained in the same way as in Example 1 was dissolved in 1,000 ml of a physiological saline. The solution was filtered aseptically by a membrane filter and the filtrate was filled in the sterilized glass containers in an amount of 10 ml for each container. With the containers stoppered, the solution was lyophilized to obtain a powdery α-amylase inhibitor.

EXAMPLE 6

Oral Tablet

First, the following components (1) to (4) were prepared:

(1) DOG2Az, 60 g (2) Mannitol, 200 g (3) Potato starch, 47 g (4) Magnesium stearate, 3 g Then, (1) and (2) were mixed, to which (3) was added as a 10% starch paste. The mixture was passed through a 60-mesh (B.S.) sieve and further screened by passing through a 16-mesh (B.S.) sieve, and the obtained granules were mixed with (4). The mixture was compressed into tablets having a diameter of 10 mm and weighing 500 mg per tablet to provide a prophylactic or therapeutic agent (oral tablet) for hyperglycemia or diabetes of the present invention.

EXAMPLE 7

Capsule 50 g of GDOG2Az, 50 g of potato starch, 50 g of lactose and 10 g of crystal cellulose were mixed well and the mixture was encapsulated to obtain the capsules for the prophylaxis or treatment of hyperglycemia or diabetes according to the present invention, each capsule containing 100 mg of active ingredient.

EXAMPLE 8

Liquid Preparation for Internal use 1 ml of benzoic acid (45 v/v ethanol) and purified water were added to 10 g of DOG2Az to make the overall amount of the solution 100 ml to obtain an internal liquid medicine for the prophylaxis and treatment of hyperglycemia or diebetes of the present invention.

EXAMPLE 9

Injection 5 g of sterilized DOG2Az was dissolved in distilled water for injection to make the overall amount of the solution 300 ml and the solution was aseptically contained in ampules at a rate of 3.0 ml per ampule to prepare an injection for the prophylaxis and treatment of hyperglycemia or diabetes of the present invention.

EFFECT OF THE INVENTION

The maltoligosaccharide derivatives represented by the formula (1) according to the present invention have a strong inhibitory activity against α-amylase and cause no side effects such as diarrhea and loose passage, so that if the present derivatives or their hydrates or physiologically acceptable salts are used as an active ingredient, there can be obtained a potent α-amylase inhibitor or prophylactic or therapeutic agent for hyperglycemia, e.g. diabetes, adiposity and the diseases caused thereby such as hyperlipidemia, fatty liver, autonomic imbalance, arteriosclerosis, cataract, etc., particularly diabetes.

What is claimed is:

1. Maltoligosaccharide derivatives represented by the general formula:

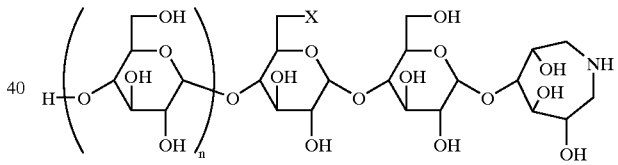

(wherein n is an integer of 0 to 3, and X is a hydrogen atom or a hydrophobic group) or their hydrates or physiologically acceptable salts.

2. The maltoligosaccharide derivatives or their hydrates or physiologically acceptable salts according to claim 1, wherein in the formula X is a hydrogen atom or a halogen atom.

3. The maltoligosaccharide derivatives or their hydrates or physiologically acceptable salts according to claim 1, wherein in the formula n is 0 or 1 and X is a hydroen atom.

4. An α-amylase inhibitor containing as an active ingredient a maltoligosaccharide derivative represented by the general formula

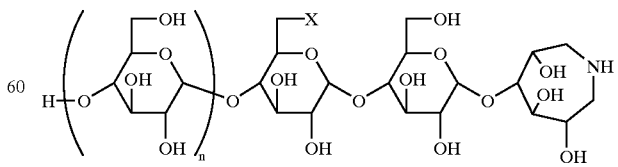

(wherein n is an integer of 0 to 3, and X is a hydrogen atom or a hydrophobic group) or its hydrate or physiologically acceptable salt.

5. An α-amylase inhibitor according to claim 4, wherein in the formula X is a hydrogen atom or a halogen atom.

6. An α-amylase inhibitor according to claim 4, wherein in the formula n is 0 or 1 and X is a hydrogen atom.

7. A therapeutic agent for hyperglycemia containing as an active ingredient a maltoligosaccharide derivative represented by the general formula:

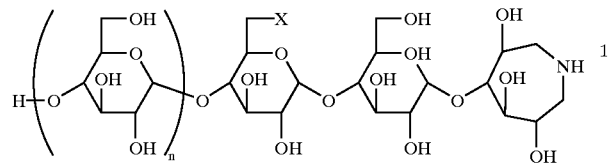

(wherein n is an integer of 0 to 3, and X is a hydrogen atom or a hydrophobic group) or its hydrate or physiologically acceptable salt.

8. A therapeutic agent for hyperglycemia according to claim 7, wherein in the formula X is a hydrogen atom or a halogen atom.

9. A therapeutic agent for hyperglycemia according to claim 7, wherein in the formula n is either 0 or 1 and X is a hydrogen.

10. A therapeutic agent for hyperglycemia according to claim 7, wherein the hyperglycemia is diabetes.

11. A therapeutic agent for hyperglycemia according to claim 8, wherein the hyperglycemia is diabetes.

12. A therapeutic agent for hyperglycemia according to claim 9, wherein the hyperglycemia is diabetes.

* * * * *